United States Patent [19]

Müller et al.

[11] 4,394,487

[45] Jul. 19, 1983

[54] ADSORBENT FOR THE AFFINITY-SPECIFIC SEPARATION OF MACROMOLECULAR MATERIALS

[75] Inventors: Werner Müller, Bielefeld; Hans Bünemann, Steinhagen, both of Fed. Rep. of Germany

[73] Assignee: Boehringer Mannheim GmbH, Mannheim-Waldhof, Fed. Rep. of Germany

[21] Appl. No.: 309,543

[22] Filed: Oct. 7, 1981

Related U.S. Application Data

[62] Division of Ser. No. 880,914, Feb. 24, 1978, Pat. No. 4,335,226.

[30] Foreign Application Priority Data

Mar. 2, 1977 [DE] Fed. Rep. of Germany ....... 2709094

[51] Int. Cl.³ .................... C08F 267/10; C08F 8/00
[52] U.S. Cl. .................................... 525/281; 525/279; 525/284; 525/293; 525/296; 525/374; 525/375; 525/378; 525/348; 525/349
[58] Field of Search ............... 525/281, 279, 296, 375, 525/374

[56] References Cited

U.S. PATENT DOCUMENTS

| | | | |
|---|---|---|---|
| 3,640,983 | 2/1972 | Horiguchi et al. | 526/306 |
| 4,017,476 | 4/1977 | Murray et al. | 260/42.21 |
| 4,035,316 | 7/1977 | Yen et al. | 526/306 |
| 4,046,750 | 9/1977 | Rembaum | 260/42.21 |
| 4,194,877 | 3/1980 | Peterson et al. | 260/42.21 |
| 4,213,860 | 7/1980 | Taibris et al. | 210/656 |

OTHER PUBLICATIONS

Khym, Analytical Biochemistry, 1976, 71 pp. 231–242.
Irman et al., Biochemistry, 1969, 8 (No. 10), pp. 4074–4082.

*Primary Examiner*—Carman J. Seccuro
*Attorney, Agent, or Firm*—Felfe & Lynch

[57] ABSTRACT

Adsorbents are provided for the affinity-specific separation of macromolecular materials, particularly biopolymers, the adsorbents comprising a polymeric carrier on to which an affine residue for the macromolecular material is covalently bound, either directly or via polymeric spacer. Preferred affine residue is comprised of a specific complex formers which are base-specific and/or structure specific for the macromolecular material. The invention also provides novel complex formers comprising a certain dyestuff residues and processes for their preparation.

7 Claims, 7 Drawing Figures

ADSORBENT FOR THE AFFINITY-SPECIFIC SEPARATION OF MACROMOLECULAR MATERIALS

This is a division of application Ser. No. 880,914, filed Feb. 24, 1978 now U.S. Pat. No. 4,335,226.

The present invention relates to the separation of macromolecular materials, particularly of biopolymers. More specifically, the invention relates to an adsorbent for the affinity-specific separation of such macromolecular materials. In a still more specific aspect, the invention relates to the separation of mixtures of one- and/or two-chained nucleic acids, especially desoxyribonucleic acids, the preparation and utilization of such adsorbent.

The isolation of individual genes or of groups of identical genes in repetitive arrangement from the genome of eukaryotic cells is of interest not only from a purely scientific point of view but is also of great practical importance from the point of view of gene technology. Such isolations were only possible when the base composition of the gene or of the gene group with their "spacers" differed by at least 6 to 7% from the average base composition of the total genome. Separation processes which have mostly been used include caesium ion density gradient centrifuging with DNA base-specific additions, such as silver, mercury or platinum ions, or actinomycin, netropsin or the dyestuff "Hoechst 33258". These processes have only a limited capacity and are expensive and time consuming.

The development of materials for the affinity chromatography of biopolymers has, in years past, considerably simplified the isolation of a large number of biopolymers or has even made the pure preparation thereof possible for the first time. In the cases of these processes, it is usual to start from a carrier material which, after chemical activation, is reacted with a substance which binds as specifically as possible with the biopolymer to be isolated. On the basis of this specificity, the desired biopolymer can, in the ideal case, be selectively adsorbed from a mixture of similar compounds on to the chromatographic material and subsequently, under appropriate conditions, can be desorbed in a pure state (see P. Cutarecasas and C. B. Anfinsen, Ann. Rev. Biochem., 40, 259-278/1971).

In spite of the considerable number of examples of the successful use of these methods, for a number of biopolymers hitherto no chromatographic material has been developed which also makes possible a similar selective and programmed separation of mixtures of nucleic acids. A high resolving fractionation of mixtures of nucleic acids on a gramme scale is, however, a prerequisite for such an isolation of individual genes or of groups of identical genes.

In the case of the available processes for the separation of nucleic acids of low molecular weight, for example of transfer ribonucleic acids, the separation is achieved in various species of adsorbents which combine ion exchange properties with lipophilic exchange actions (see M. Kothari and V. Shankar, J. Chromatography, 98, 449-475/1974). The exchange action possibilities of the carrier with the rare bases of the nucleic acids, which are present in varying amounts in the various transfer ribonucleic acids, are thereby utilised.

Since, as a rule, the high molecular weight ribonucleic acids and desoxyribonucleic acids do not contain any rare bases, methods for the separation thereof can only be built upon the following characteristic differences:

(a) ratio of single to double chain
(b) differences in the base composition
(c) differences in the base sequence
(d) differences in the molecular weights
(e) differences in the tertiary structures.

All these characteristic features are, in fact, utilized in conventional methods of fractionation (see R. M. Kothari, Chromatog. Rev., 12, 127-155/1970).

In the case of the most effective methods, differences according to b, c and e lead, in the fractionation in the salt gradients, to differences in the suspension density for the individual DNA species which can be still further increased by the addition of base specific substances. The sharpness of separation decreases with decreasing molecular weight and the capacity with increasing molecular weight. In the case of adsorption chromatography on hydroxyapatite, fractionation takes place essentially according to a and only to a limited extent according to b, guanine-cytosine-rich nucleic acids already being desorbed at somewhat lower salt concentrations than the adenine-thymine-rich components (see W. Pakroppa and W. Müller, Proc. Nat. Acad. Sci. USA, 71(3), 699-703/1974).

Analogously, double chain nucleic acids can also be fractionated on specific protein-keiselguhr adsorbents (for example methyl serum albumin-keisulguhr) according to differences of the base composition, the guanine-cytosine-rich DNA species being eluted first (see J. D. Mandell and A. D. Hershey, Analytical Biochemistry, 1, 66-77/1960; N. Sueoka and Ts'ai-Ying Cheng, J. Mol. Biol., 4,161-172/1962). The actual manner of working of these rather accidentally discovered adsorbents is not known. Therefore, the low sharpnesses of separation of these materials have hitherto not been fundamentally improved, in spite of all attempts to do so.

Only in recent years have there been found, in the case of the systematic investigation of numerous substances which form complexes with nucleic acids, compounds which appear to be suitable for a directed synthesis of materials for affinity chromatography (see W. Müller and D. M. Crothers, Eur. J. Biochem., 54, 267-277/1975; W. Müller, H. Bünemann and N. Dattagupta, Eur. J. Biochem., 54, 279-291/1975; and W. Müller and F. Gautier, Eur. J. Biochem., 54, 385-394/1975). The advantages provided by using such well investigated substances for the separation of mixtures of nucleic acids has already been demonstrated by the combined use of hydroxyapatite and ethidium bromide as base specific addition for the separation of superhelical and helical DNA (see W. Pakroppa, W. Goebel and W. Müller, Analytical Biochemistry, 67, 372-383/1975) and of hydroxyapatite in combination with phenyl neutral red derivatives as base specific complex formers for the separation of double chained DNA species (see W. Pakroppa and W. Müller, Proc. Nat. Acad. Sci. USA, 71(3), 699-703/1974).

The resolving properties of these last-mentioned methods is comparable with that of a preparative caesium chloride density gradient method, i.e. DNA fractions with differences in the (G+C) content (G stands for guanine and C for cytosine) can be separated from one another. In spite of the high capacity, this process has the disadvantages that DNA mixtures with an average molecular weight of the components of more than $20 \times 10^6$ can no longer be readily dealt with and that the special hydroxyapatite employed as adsorbent must itself be prepared.

It has been known for a long time that under certain conditions, nucleic acid mixtures can be separated in the polyethylene glycol-dextran system into RNA and single chained DNA, on the one hand, and into double chained DNA, on the other hand. The double chained DNA thereby always becomes enriched in the lighter polyethylene glycol phase, i.e. it possesses a higher partition coefficient than the single chained nucleic acids. The absolute values of the partition coefficients can admittedly be varied by about 3–4 factors of 10 by the addition of potassium and lithium salts but a fractionation according to the base composition is not successful in these systems.

It is an object of the present invention to provide adsorbents with which can be achieved a base- and/or structure specific separation of biopolymers and especially of mixtures of single chained and/or double chained and/or supercoiled and/or linear nucleic acids, especially of DNA mixtures, with a high capacity.

Affinity specificity is here to be understood to mean, in particular, structural specificity and base specificity.

We have found that this object can be achieved with an adsorbent which comprises a polymeric carrier material to which is covalently bound, directly or via comparatively long intermediate groups (spacers), an affine residue for the biopolymer or a base and/or structure-specific group.

Therefore, the present invention provides an adsorbent for the affinity specific separation of macromolecular materials, especially of biopolymers, such as nucleic acids, which comprises a polymeric carrier material to which is covalently bound, directly or via a polymeric "spacer", an affine residue for the biopolymers.

According to an especially preferred embodiment of the present invention, there is provided an adsorbent of the defined type which comprises a small-pored, low compressable, polymeric carrier material on to which is grafted a copolymer of at least two co-polymerizable monomers, one of which carries an affine residue for the biopolymer.

As affine residues for the biopolymer, there can be used base- and/or structure-specific complex formers, which are described in the above-mentioned literature references. In particular, there can be used residues of dyestuffs of the following general formulae (I) and (II):

(I)

(II)

in which X is a CH group or a nitrogen atom, Y is an oxygen or sulphur atom or an NH group or a group of the general formula:

each $R^1$, independently of one another, is a hydrogen atom or a methyl radical, $R^2$ is a hydrogen atom or a methyl radical, $R^3$ is a hydrogen atom or a methyl radical, $R^4$ is a hydrogen atom or a methyl radical and $A^\ominus$ is an anion, such as a chlorine anion, a perchlorate anion or an oxalate anion.

Examples of base- and/or structure-specific complex formers which, according to the present invention, are especially preferably bound on to the polymeric carrier material, include the residues of the following dyestuffs:

1. diamidinophenyl-indole (DAPI)

2. malachite green 3. crystal violet 4. methyl green 5. auramine

6. Hoechst Dyestuff No. 33258

7. Di-tert-butyl-proflavine

8. Di-tert.-butyl-acriflavine

9.

10.

11.

12.

13.

14.

15.

16.

17.

18.

19.

20. Proflavine

21.

22.

23.

24.

25. Thionine

26. Acridine orange

27. Pyronine G

28. Thiopyronine

29.

30.

31. methylene blue

32.

33. ethidium bromide

However, according to the present invention, the most preferred base- and/or structure-specific complex formers are phenyl neutral red of the formula:

and malachite green of the formula:

These dyestuffs are known and are commercially available or can be prepared by processes which are well known to the art skilled and are described, for example, in the above-mentioned publications of W. Müller and D. M. Crothers (Eur. J. Biochem., 54, 267–277/1975), W. Müller, H. Bünemann and N. Dattagupta (Eur. J. Biochem., 54, 279–291/1975) and W. Müller and F. Gautier (Eur. J. Biochem., 54, 385–394/1975).

These base- and/or structure-specific complex formers or dyestuff residues can be covalently bound to the carrier material by methods which are well known to the art skilled, for example by esterification with hydroxyl groups present on the carrier material via carboxyl groups introduced into the dyestuffs molecule, by amide formation, by urethane formation or also by copolymerization in the absence or preferably in the presence of other copolymerizable monomers via copolymerizable double bonds which are introduced into the dyestuff molecule, for example via an acrylamide group, such as is the case with acrylic-phenyl neutral red and acrylic-malachite green of the following formulae which, according to the present invention, are preferred as base- and/or structure-specific complex formers. These designations are trivial names, the exact designations being acryloylaminophenyl neutral red and acryloylaminomalachite green:

These base- and/or structure-specific complex formers can be prepared by the art skilled in known manner by the introduction of the acrylic radical into the dye-stuff molecules. This also applies to the other dyestuff molecules mentioned hereinbefore.

The term acrylic radical has, in the present cases, the same meaning as the term acryloyl radical.

The preparation is preferably carried out by the processes described in the following Examples 3 and 4. The acryloyl dyestuffs are new.

According to the present invention, as polymeric carrier material there is preferably used a small pored, low compressability polymeric carrier material, such as poly-bisacrylamide, the small pored and low compressibility polymeric carrier materials having proved to be very advantageous for the affinity chromatography of highly viscous nucleic acid solutions. Furthermore, these polymeric carrier materials do not exhibit any strong exchange actions with the affine residues, especially with the base- and/or structure-specific complex formers for nucleic acids which are bound to the polymeric carrier material either directly or via polymeric spacers.

It has proved to be advantageous to introduce, between the polymeric carrier material and the base- and/or structure-specific complex former, a comparatively long spacer, i.e. a comparatively long molecular chain without functional groups, since complex formation of the base- and/or structure-specific complex former with the helical nucleic acid is hereby not impaired by steric hindrance.

Therefore, it is especially advantageous when, in the adsorbent according to the present invention, the affine residue for the biopolymer or the base- and/or structure-specific complex former is bound to the polymeric carrier material via a copolymer which preferably has a degree of polymerization of from 200 to 300. For the formation of this copolymer, it is preferable to use a further monomer which is copolymerizable with the group introduced for the polymerization into the base- and/or structure-specific complex former and with the copolymerizable groups present on the polymeric carrier material.

This further monomer is preferably acrylamide and the above-mentioned acrylic radical-containing dyestuffs are grafted on to a poly-bisacrylamide which still has free, copolymerizable double bonds.

The present invention is also concerned with a process for the preparation of the above-mentioned adsorbents, wherein there is first formed the polymeric material by polymerization or by polycondensation of at least one monomer which, in addition to the functional group necessary for the polymerization or polycondensation, has a further functional group via which the affine residue for the bipolymer can be bound directly or via a polymeric spacer, this polymeric carrier material is optionally comminuted to the desired particle size and then the affine residue for the biopolymer is grafted on either directly or by copolymerization in the presence of at least one further monomer as comonomer.

Grafting on can take place in any desired manner, for example by esterification, amide formation or urethane formation, using conventional reagents and conventional reaction conditions or there are introduced into the polymeric carrier material the groups suitable for these reactions or there are introduced the affine residues for the biopolymer.

However, it is also possible to graft the affine residues for the biopolymer, into which has been introduced a copolymerizable double bond, in the presence of an excess of a further copolymerizable monomer as comonomer, on to poly-bisacrylamide since poly-bisacrylamide still contains free, copolymerizable double bonds. The graft copolymerization can be carried out in water or in an inert organic solvent and in the presence of a conventional polymerization catalyst.

The copolymerizable affine residue for the biopolymer is preferably acrylic-phenyl neutral red or acrylic-malachite green and the further copolymerizable monomer is preferably acrylamide, a copolymer of these components being grafted on to poly-bisacrylamide. According to a preferred method of working, a copolymer of acrylamide and acrylic-phenyl neutral red or acrylic-malachite green with a degree of polymerization of 200 to 300 is grafted on.

In the case of this graft copolymerization, it is preferable to work with a ratio of the affine residue for the biopolymer having a copolymerizable double bond to the further copolymerizable monomer of 1:100 to about 1:500, this reaction more preferably being carried out with a ratio of about 1:300. We have also found that the molar ratio of the further monomer to the affine residue for the biopolymer having a copolymerizable double bond is also retained in the copolymer. In the case of an average degree of polymerization of the copolymer of 200 to 300, it is possible for the grafted on copolymer chains each to bear only one affine residue for the biopolymer. The copolymers thus form spacers of differing length between the affine residue for the biopolymer and the polymeric carrier material, especially the poly-bisacrylamide particles.

We have found that the adsorbents according to the present invention fulfilled the desired requirements and can be obtained synthetically without difficulty and in a simple manner. For example, the polymeric carrier material can be obtained by the polymerization of bisacrylamide in a highly concentrated solution. The polymerization product is a btittle, colorless solid body which can be very easily comminuted to give readily sedimenting particles which, by several sievings, can be homogenized to give the desired particle size. The swelling behavior in aqueous solution is constant, even in the case of extreme salt concentrations, and is practically independent of the flowthrough rate in the case of chromatography. Since these particles still contain a number of unreacted polymerizable double bonds, they can, as already explained above, be used for the further graft polymerization.

Thus, with the adenine-thymine-specific acrylic-malachite green and with the guanine-cytosine-specific acrylic-phenyl neutral red, there are obtained with acrylamide in the presence of these poly-bisacrylamide particles, by copolymerization in aqueous solution, the adsorbents which are preferred according to the present invention. 40 to 50% of the formed copolymer with an average degree of polymerization of about 200 are thereby bound under the usual reaction conditions in the form of graft copolymers on to the carrier particles of the polybisacrylamide. After thorough rinsing, the strongly colored adsorbent particles no longer give off any dyestuff and they can then be used directly for the affinity chromatography of nucleic acids. The mixture of nucleic acids is usually adsorbed in 0.01 M phosphate buffer on to the material and desorbed with a linear salt gradient, the nature of the salt depending upon the nature of the nucleic acids. Whereas for the desorption of ribonucleic acids, including transfer-ribonucleic acids, it is sufficient to use sodium chloride, for the base-specific elution of DNA from acrylic-malachite green-containing adsorbents, perchlorate is necessary.

We have found that for the preparation of the carrier material, it is also possible to start from insoluble materials containing hydroxyl or amino groups which are present in pearl form, for example aminoalkyl-Sepharose, microcrystalline cellulose, cross-linked hydroxyethyl methacrylate or epoxypropyl acrylate. In the case of these carriers, the acrylic groups necessary for subsequent grafting are introduced by reaction with acryloyl chloride. Thus, there can be achieved a high loading with dyestuff similar to that in the case of the grafting from acrylamide fragments.

Thus, the present invention is also concerned with the use of the said adsorbents for the separation of biopolymers by two-phase affinity partitioning, by two-phase partition chromatography, by gel electrophoresis and especially by affinity chromatography. These adsorbents can also be advantageously used for the separation of mixtures of one-chain and/or two-chain nucleic acids and especially of DNA mixtures.

Since the adsorbents according to the present invention, which carry base- and/or structure-specific complex formers on the basis of 5-phenyl-phenazonium salts, act specifically for guanine-cytosine-rich DNA and the adsorbents according to the present invention which act as base- and/or structure-specific complex formers on the basis of triphenylmethane dyestuffs act specifically for adenine-thymine-rich DNA, the desired base- and/or structure-specific or sequence specific separations of mixtures of nucleic acids can be carried out. Predominantly struture-specific complex formers can be compounds capable of intercalation. By intercalation, there is to be understood, in particular, a special exchange of dyestuff molecules with DNA, the dyestuff molecule thereby slipping between two neighboring base pairs of the DNA double helix. Which substances are capable, due to their structure, of intercalation is known to the skilled artisan. They can be planar, electron-rich chromophors and, in particular, can be the residues of planar, polycylic ring systems, such as bi-, tri- or tetracyclic, condensed ring systems, which can contain heteroatoms, such as nitrogen, oxygen or sulfur.

The effect can be increased when, for example, in the case of ethidium bromide or of 9-(acryloylaminoethylamino)-2-methoxy-6-chloroacridine, an amino group is present on the ring system which makes possible a binding on to the phosphate groups of the DNA. It is a simple matter for one skilled in the art to use correspondingly useful compounds, for example, acridines, benzacridines, phenanthrenes, phenantridines, pyridoindoles, naphthalenes, naphthothiophenes, benzothiophenes, thianthrenes, xanthines, phenoxanthines, quinolines, quinoxalines, phenanthrolines, phenothiazines, phenoxazines, phthalazines and the like.

Figure 7:
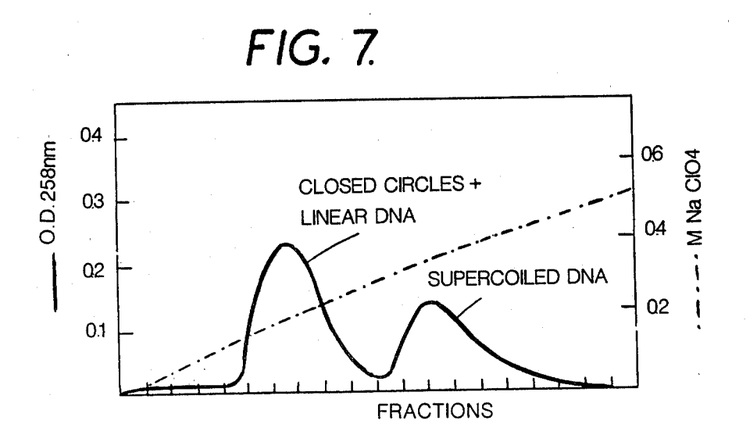
FIG. 7 shows the elution diagram for the separation of supercoiled and linear DNA.

Acridine derivatives, for example 9-(acryloylaminoethylamino)-2-methoxy-6-chloroacridine, or phenanthridine derivatives, for example ethidium bromide (5-ethyl-3,8-diamino-6-phenyl-phenanthridium bromide), separate, after coupling thereof to bis-acrylamide particles, base-nonspecific double-chained DNA from supercoiled DNA (see elution diagram 7 of the accompanying drawings). This is very important for a simple separation of plasmid and viral DNAs from cell digests, a column replacing the laborious ethidium bromide-caesium chloride gradients. This separation can also be carried out with an acryloylaminophenyl-neutral red column since both dyestuffs form a complex-like structure (intercalation complex) with the DNA. Acryloylamino-phenyl neutral red separates not only structurally-specifically but also base-specifically. Therefore, depending upon the particular separation problem, a series of variations is possible with regard to the composition of the adsorbent.

Since the base- and/or structure-specific complex formers are bound via a stable covalent carbon-carbon bond, the adsorbents according to the present invention can also be used at more extreme pH values, washed with detergents and regenerated with salt solutions. Furthermore, it is also possible to incorporate several different base- and/or structure-specific complex formers or monomers so that adsorbents can be formed which can be used for the separation of transfer ribonucleic acids. The chain length of the grafted-on copolymers and thus the length of the chain between the polymeric carrier material and the base- and/or structure-specific complex former can be controlled in the usual manner by the use of mercaptoethanol In the following, the present invention is explained in more detail with reference to specific Examples and to the accompanying drawings, in which:

The following Examples are given for the purpose of illustrating the present invention:

EXAMPLE 1

(A) Preparation of the poly-bisacrylamide carrier material.

50 g. N,N'-Methylene-bisacrylamide are suspended in 100 ml. methanol in a tall 1 liter polyethylene beaker and mixed with 200 ml. boiling double distilled water. Upon stirring the mixture with a magretic stirrer, the bisacrylamide goes completely into solution. The solution is cooled to 60° C. and, while stirring intensively, there is first pipetted in 1 ml. N,N,N',N'-tetramethylethylenediamine and then, all at once, a solution of 0.2 g. ammonium peroxide disulphate in 5 ml. water. Immediately after mixing up, the stirrer is switched off. After a few seconds, the solution becomes turbid and solidifies to a colorless block upon heating. Polymerization is stopped after about 1 minute by coarsely comminuting the block with a large spatula. The pieces obtained are suspended in 1 liter methanol in a 2 liter polyethylene beaker and comminuted to a granular slurry. For the further homogenisation of the particles, the slurry is successively rubbed through sieves of decreasing mesh size (1 mm.×1 mm.; 0.5 mm.×0.5 mm.; and 0.25 mm.×0.25 mm.). The resulting pieces are allowed to sediment, whereupon the milky-turbid supernatant is decanted off. This procedure is repeated several times, first with methanol, then with a methanol/water mixture, subsequently with a 1% acetic acid solution and finally with distilled water. The polybisacrylamide particles obtained are stored in aqueous solution and can be used at any time for the graft polymerization described in the following.

From 300 ml. of the polymerization solution, there are obtained about 300 ml. of deposited poly-bisacrylamide particles.

(B) Grafting of a copolymer of acrylamide and acrylic-phenyl neutral red on to the poly-bisacrylamide obtained in Stage A.

60 ml. of the deposited poly-bisacrylamide particles obtained in Stage A are suspended in 20 ml. distilled water in a flask provided with a screw closure. In this suspension there are dissolved 5 g. acrylamide and 10.3 mg. acrylic-phenyl neutral red chloride, for which purpose the suspension in the flask is carefully shaken until the dyestuff has dissolved completely. The copolymerization is then initiated by the addition of 0.050 ml. mercaptoethanol for the adjustment of the degree of polymerization and 1 ml. of a sodium peroxide solution (0.8 g. sodium peroxide in 100 ml. 1 M sodium acetate buffer with a pH value of 5.5) as catalyst. The suspension formed is immediately gassed for 5 minutes with nitrogen and then maintained at ambient temperature with the exclusion of air. After about 30 minutes, the reaction mixture warms up noticeably and after about 2 hours the polymerization is substantially finished. The reaction mixture is left to stand for several hours before transferring the viscous suspension to a suction filter. The viscous, deep colored solution is filtered with suction and the dark colored particles remaining behind on the filter are thoroughly washed with water until the wash solution, even when using a 1% acetic acid solution, remains colorless. After a subsequent continuous rinsing overnight with 0.01 M sodium phosphate buffer with a pH value of 6.0, the material obtained can be used for the affinity chromatography of nucleic acids.

The determination of the yield is carried out, in the case of acrylamide, by means of a $^{14}C$ marking and, in the case of the dyestuff, by means of the optical density. The yields are as follows:

| dyestuff: | incorporation into the copolymer (bound and unbound): | 60.5% |
|---|---|---|
| acrylamide: | incorporation into the copolymer (bound and unbound): | 49.2% |
| dyestuff: | incorporation into the bound copolymer, referred to the total: | 51.0% |
| acrylamide: | incorporation into the bound copolymer, referred to the total: | 57.0% |

It can be ascertained that the molar starting ratio of dyestuff to acrylamide (1:3000) is also retained in the copolymer obtained. Since the average degree of polymerization of the copolymer is determined as being 200 to 300, it can be deduced therefrom that the copolymer chains each carry only one dyestuff molecule per chain.

Figure 1:
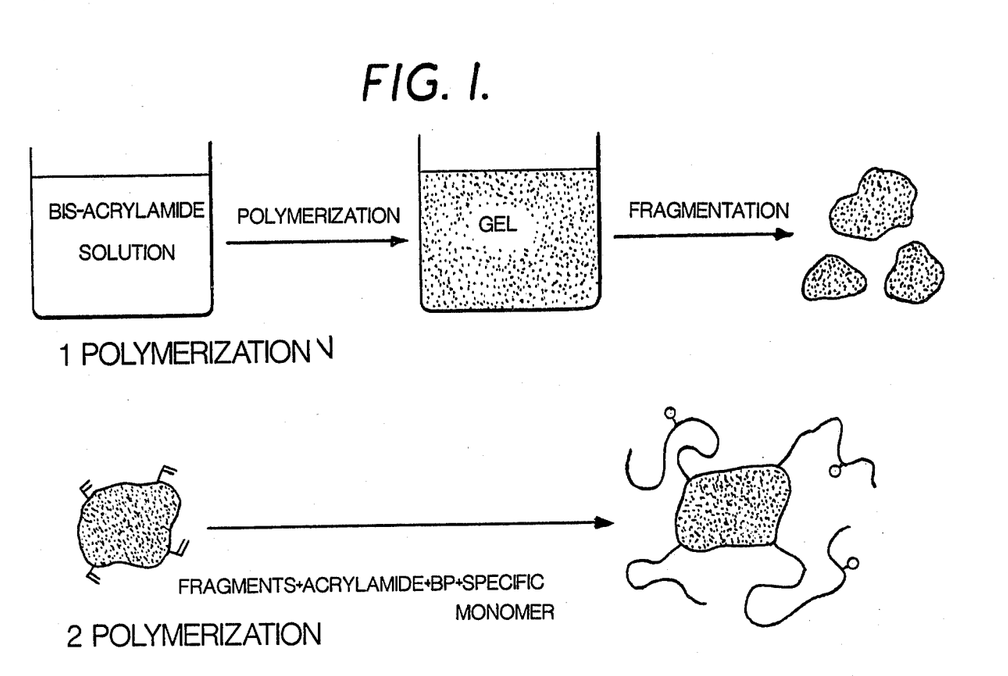
FIG. 1 is a scheme for the preparation of adsorbents which are especially preferred according to the present invention by a two-stage polymerization.

The above-described process is illustrated schematically in FIG. 1 of the accompanying drawings.

EXAMPLE 2

Separation of mixtures of nucleic acids by affinity chromatography on adsorbents according to the present invention.

As is shown in the elution diagrams in FIGS. 2 to 6 of the accompanying drawings, the possibilities of use of the adsorbents according to the present invention in the field of nucleic acid fractionation is very versatile. Depending upon the base specificity of the bound dyestuff, mixtures of double-chained nucleic acids can be separated according to their base composition.

Figure 2:
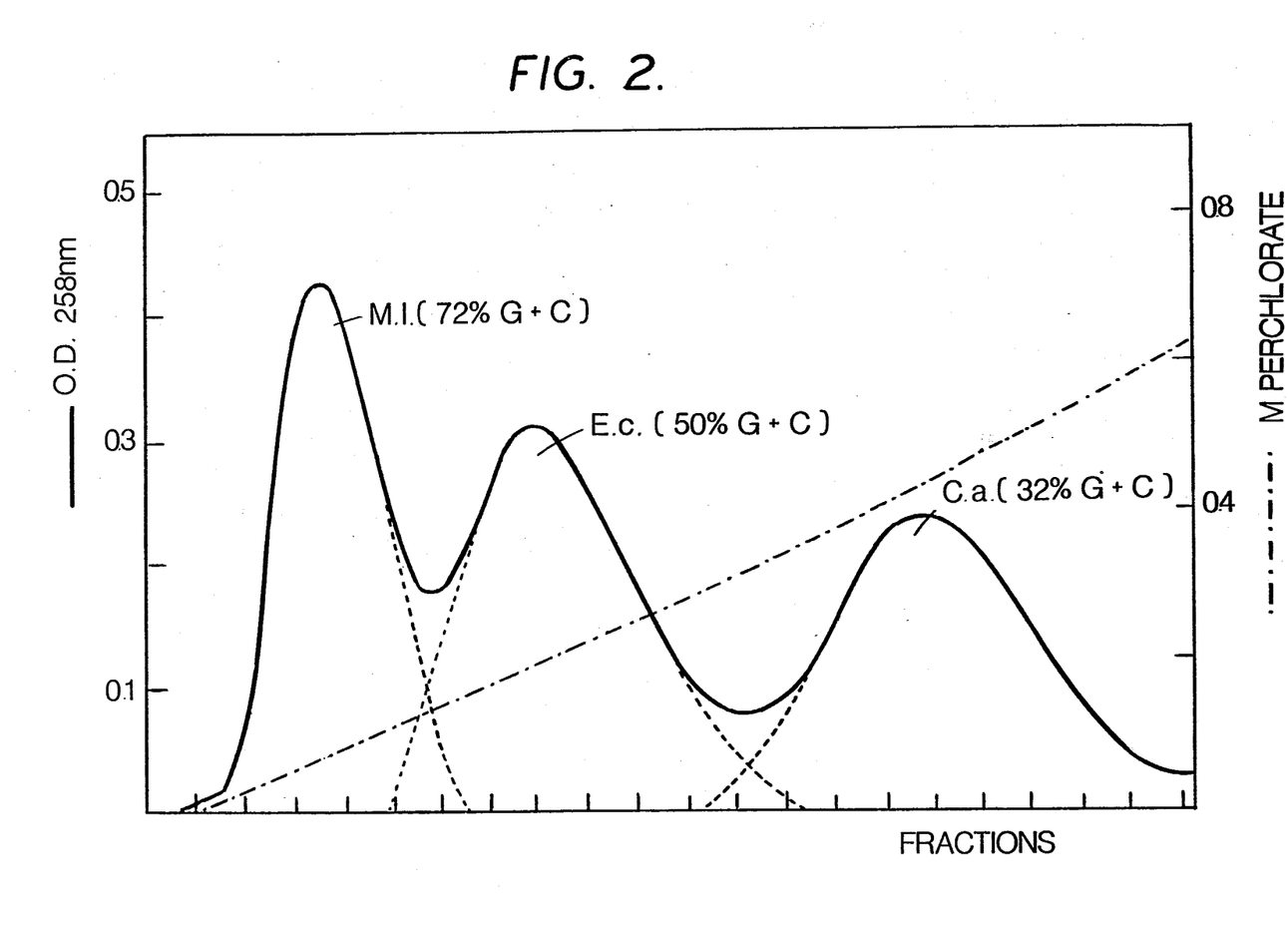
FIG. 2 shows the elution diagram of a mixture of three sheared, bacterial desoxyribonucleic acids with the use of an adsorbent according to the present invention.

Thus, FIG. 2 of the accompanying drawings shows the elution diagram of a mixture of three sheared bacterial desoxyribonucleic acids with an average molecular weight of about 700,000 D with differing base composition. For this purpose, use is made of a column with the dimensions 16 cm.×1.5 cm. which, as adsorbent, contains acrylicmalachite green-acrylamide copolymer grafted on to polybisacrylamide particles, the amount of desoxyribonucleic acid used being about 1 mg.

Figure 3:
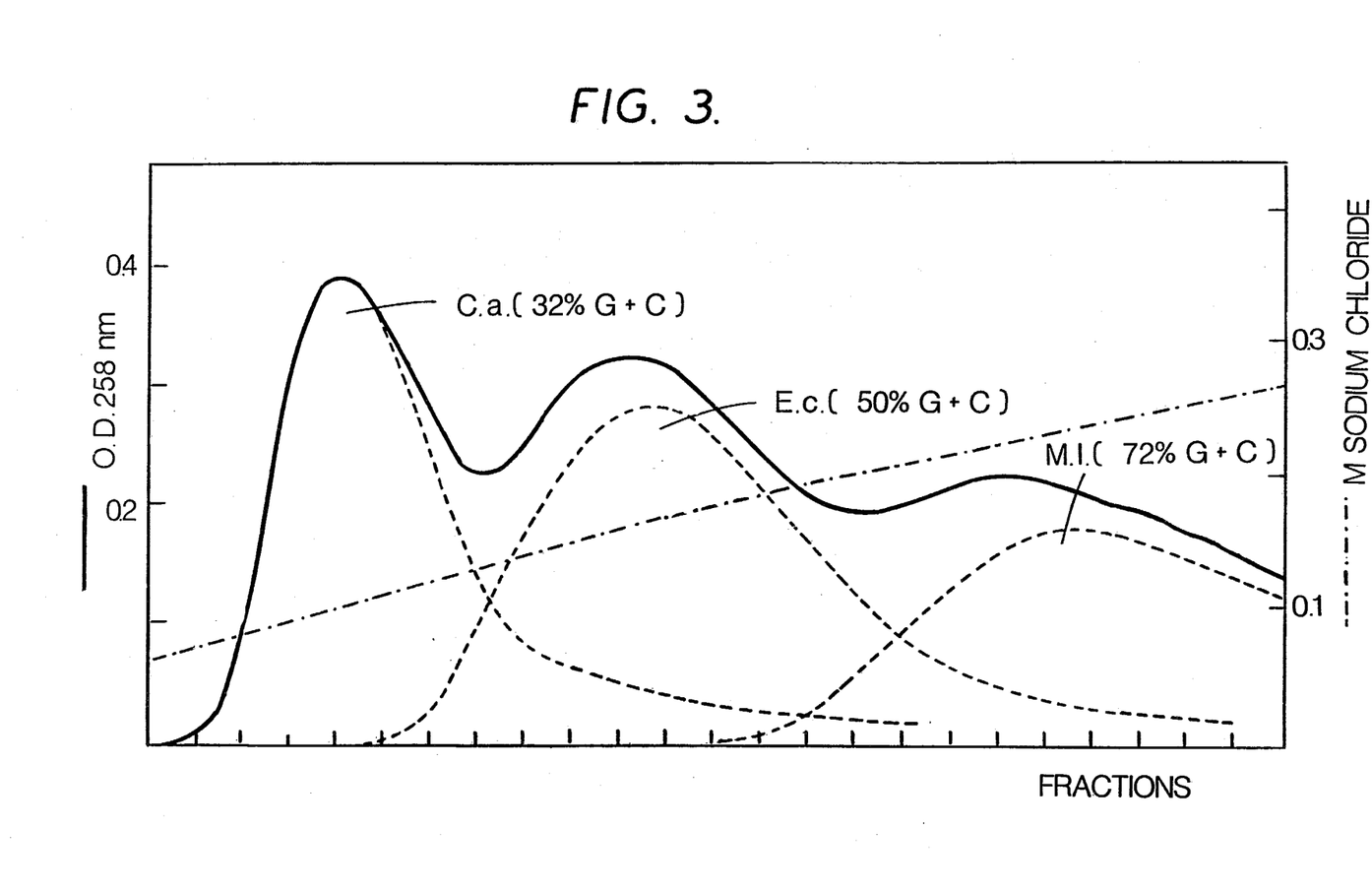
FIG. 3 shows the elution diagram of a mixture of three sheared, bacterial desoxyribonucleic acids which have been obtained with the use of another absorbent according to the present invention.

FIG. 3 of the accompanying drawings shows the elution diagram of a mixture of three sheared bacterial desoxyribonucleic acids with an average molecular weight of about 700,000 D which have a differing base composition. For the elution of 1 mg. of the nucleic acid mixture, use is made of a column with the dimensions 15.2 cm.×1.5 cm. which, as adsorbent, contains bisacrylamide particles on to which have been grafted the acrylic-phenyl neutral red acrylamide copolymer.

Figure 4:
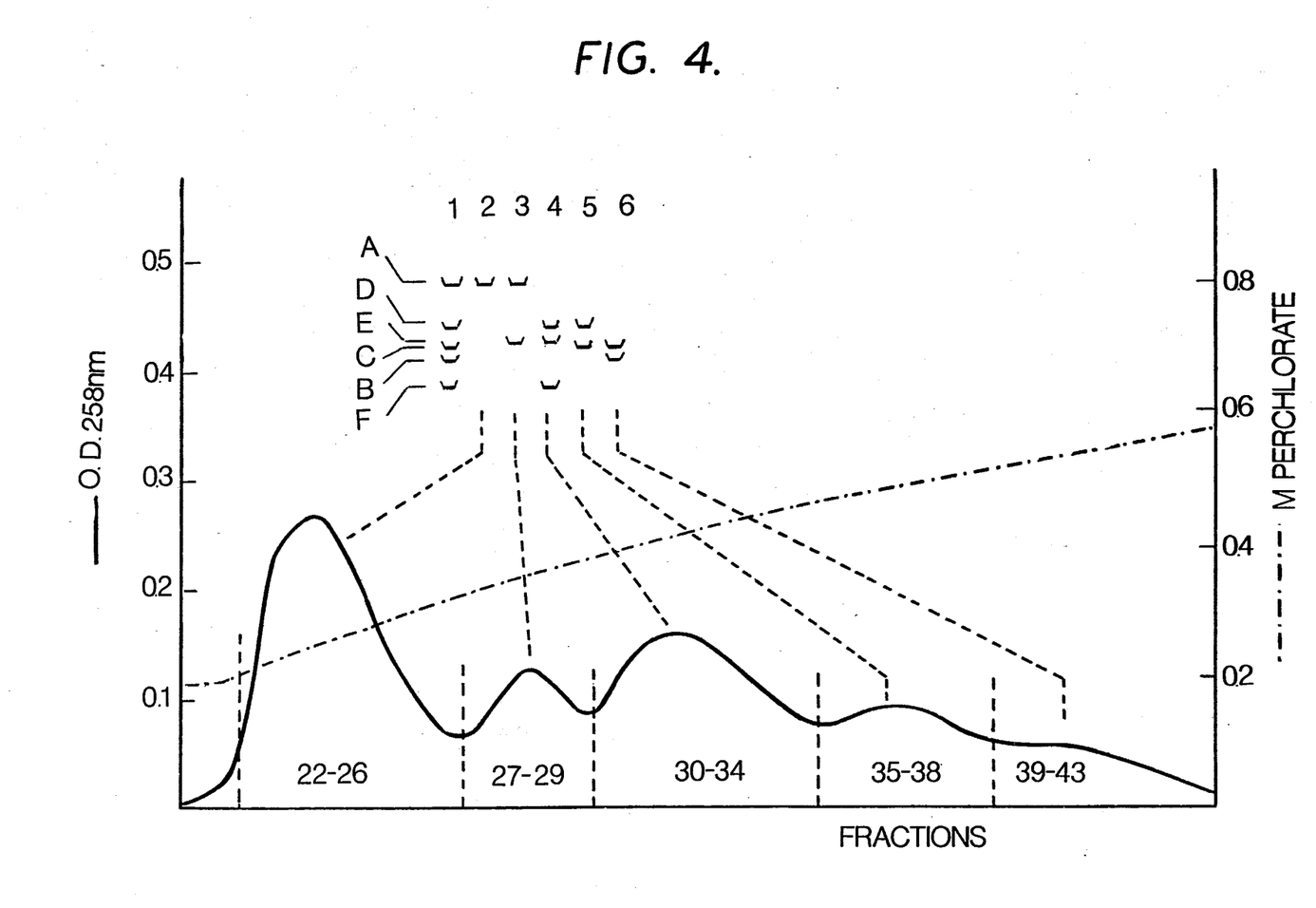
FIG. 4 shows the elution diagram of an EcoRI hydrolysate of λ-phase desoxyribonucleic acid which was obtained with the use of an adsorbent according to the present invention.

With the use of the adsorbents according to the present invention, it is also possible to fractionate DNA fragments which have been obtained by the action of restriction endonucleases. This is shown in FIG. 4 of the accompanying drawings which illustrates the elution diagram of an EcoRI hydrolysate of λ-phage desoxyribonucleic acid which is separated in an amount of 0.5 mg. with the use of a column with the dimensions 15.8 cm.×1.5 cm. which, as adsorbent, contains poly-bisacrylamide particles on to which have been grafted acrylic-malachite green-acrylamide copolymer. The characteristics of the DNA fragments set forth in FIG. 4 hereof, which shows the results of a gel-electrophoretic separation for the individual fractions, in comparisons with the starting material corresponds to the characteristics set forth in the publication of Thomas and Davis in J. Mol. Biol. 91, 315–328 (1975).

Figure 5:
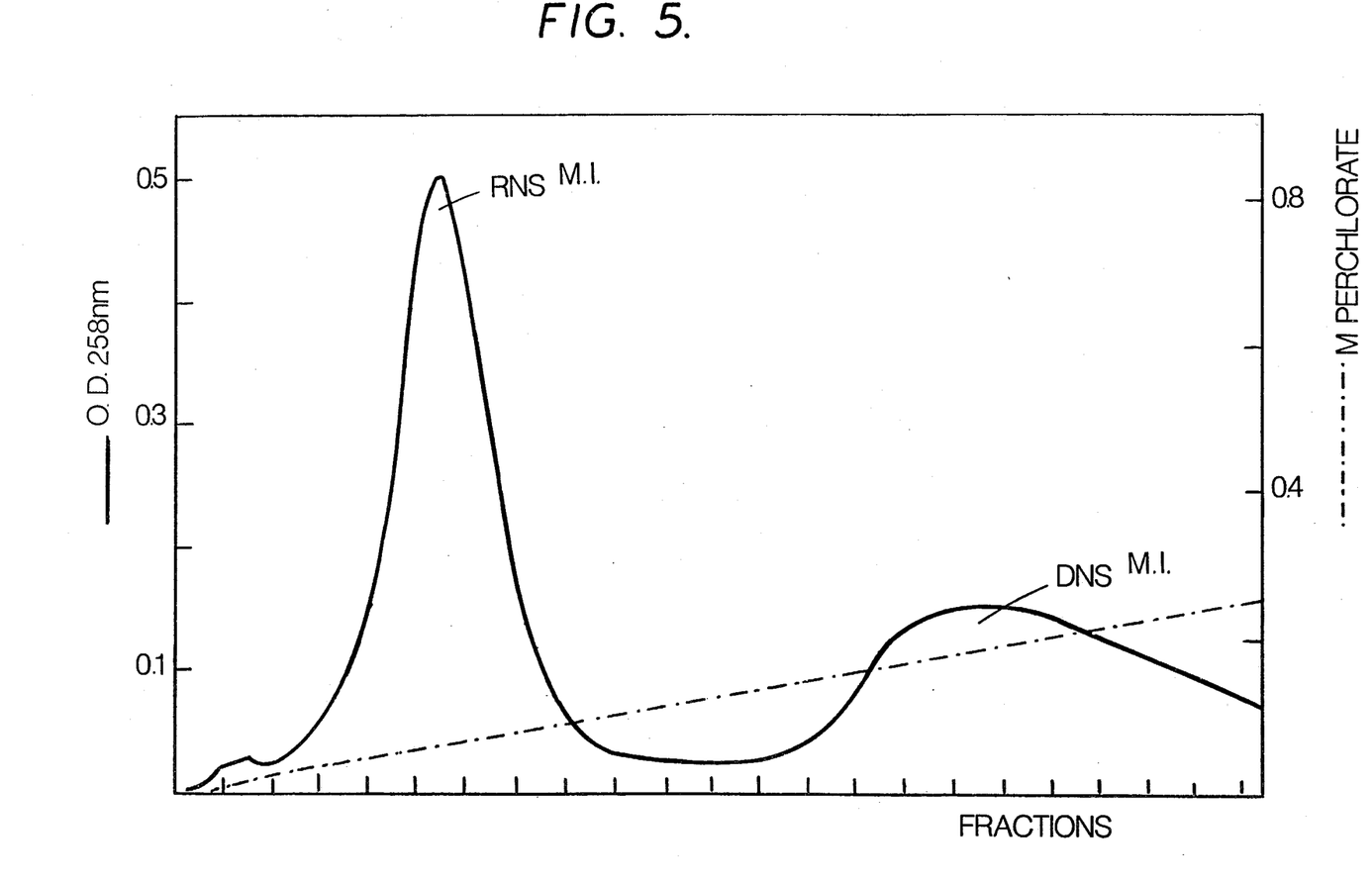
FIG. 5 shows the elution diagram which was obtained with the use of an adsorbent according to the present invention for the separation of a DNA-RNA mixture obtained by the digestion of *M. luteus*.

The separation of ribonucleic acids from desoxyribonucleic acids of the same organism also takes place smoothly with the use of the adsorbents according to the present invention, as can be seen from FIG. 5 of the accompanying drawings. This FIG. 5 shows the elution diagram of a DNA-RNA mixture from a digest of M. luteus (72% G+C), the mixture being separated in an amount of 1 mg. with the help of a column with the dimensions 16.2 cm×1.5 cm. which is packaged with poly-bisacrylamide particles on to which have been grafted the acrylic-malachite green copolymers.

Figure 6:
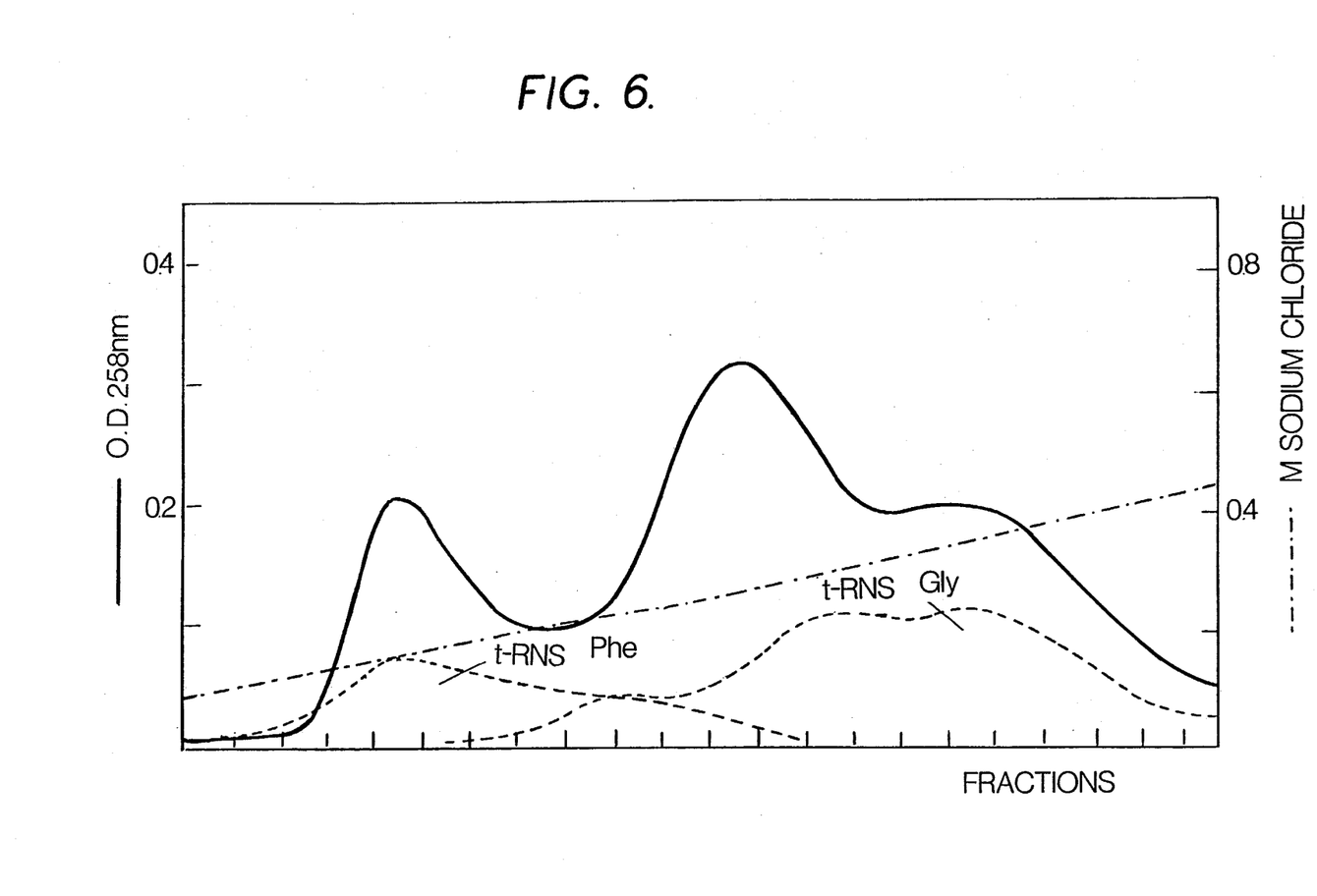
FIG. 6 shows the elution diagram of a mixture of four different transfer-ribonucleic acids from yeast which has been obtained with an adsorbent according to the present invention.

FIG. 6 of the accompanying drawings shows the elution diagram of a mixture of four different transfer ribonucleic acids obtained from yeast. The mixture, which is used in an amount of 1.5 mg., is a mixture of t-RNA$^{Phe}$, T-RNA$^{Lys}$, T-RNA$^{Glu}$ and t-RNA$^{Gly}$. For the affinity chromatography, use is made of a column with the dimensions 16 cm.×1.5 cm. which is packed with poly-bisacrylamide particles on to which have been grafted the acrylic-phenyl neutral redacrylamide copolymers.

FIG. 7 of the accompanying drawings shows the elution diagram for the separation of supercoiled and linear DNA. For the affinity chromatography, use is made of polybisacrylamide particles on to which 9-(acryloylaminoethylamino)-2-methoxy-6-chloroacridine particles have been grafted.

When using adsorbents according to the present invention in the manner described above for the separation of mixtures of nucleic acids by affinity chromatography, as elution agents there can be used aqueous salt concentration gradients, for which purpose the salt preferably used is an alkali metal salt, such as sodium chloride, sodium perchlorate, lithium perchlorate or the like. In certain cases, buffers can also be used, for example phosphate buffer: for adsorption agents which, as basespecific complex former, contain the residue of malachite green, there is used a weakly acidic buffer with a pH value of 5.5 to 6, for example a 0.01 molar phosphate buffer with a pH value of 5.5 to 6.

The requirements for the achievement of optimum salt gradients, their components, concentrations and pH values and the buffers necessary therefor can be determined without difficulty by the art skilled.

Thus, to summarize, the adsorbents according to the present invention are outstandingly suitable for the affinity-specific separation of macromolecular materials and especially of biopolymers, such as mixtures of nucleic acids. These adsorbents can be prepared in a simple manner and can be readily adjusted with regard to their base specificity.

EXAMPLE 3

Preparation of acryloylamino-malachite green.

(a) 15.1 g. (0.1 mol) 4-Nitrobenzaldehyde, 36.3 g. (38 ml.) (0.3 mol) N,N-dimethylaniline and 40.5 g. anhydrous zinc chloride are mixed and heated to a bath temperature of 100° C. The initially readily stirrable mixture becomes, during the course of the reaction, a solid green mass which can no longer be stirred. After a reaction time of 5 hours, the reaction mixture is allowed to cool. The product is taken up in 150 ml. acetone and, after stirring for some time, the product dissolves and the zinc salt separates out. The insoluble salt is filtered off with suction and washed with acetone and the filtrate is mixed with such a quantity of water that crystallization commences. The crystals are filtered off with suction and washed with water, isopropanol and diethyl ether. The yield is 28.7 g. (76.6% of theory); m.p. 168° C. The substance is sensitive to light.

(b) 3.75 g. (0.01 mol) of the nitro compound obtained according to (a) are dissolved in 200 ml. glacial acetic acid (99%) and 20 ml. water and mixed with 4 g. zinc chloride. Subsequently, 20 g. zinc dust are added portionwise at ambient temperature (20°–30° C.), with stirring and cooling. The reaction mixture is stirred for 30 minutes at ambient temperature and thereafter excess zinc is filtered off with suction and washed with glacial acetic acid. The filtrate is evaporated in a vacuum at 50° C., the residue is dissolved in 150 ml. chloroform and 100 ml. water and separated and subsequently the chloroform phase is shaken with 80 ml. 2 N aqueous sodium carbonate solution and 100 ml. water. The chloroform phase is separated off and dried over anhydrous sodium sulphate and then filtered, whereafter the filtrate is concentrated in a vacuum at 50° C. to about 100 ml. and further reacted directly (pale violet solution).

(c) The 100 ml. of chloroform solution of the amino compound thus obtained is mixed with 50 ml. methanol. 10 g. anhydrous sodium carbonate and a spatula tip of 1,3-dinitrobenzene are added thereto and subsequently, with stirring and ice cooling (0°–5° C.), 1.81 g. (1.65 ml.) acrylol chloride (double the molar amount) are added thereto dropwise. The suspension is stirred overnight at ambient temperature, thereafter the sodium carbonate is filtered off with suction and the filtrate is evaporated in a vacuum at 35°–40° C. The residue is taken up in 100 ml. chloroform and 50 ml. water and shaken and the chloroform phase is separated off, subsequently extracted with 50 ml. water, dried with anhydrous sodium sulphate and evaporated in a vacuum at 35°–40° C. The oily, greenish residue obtained is triturated with 20 ml. isopropanol and placed in the cold to crystallize. The crystals obtained are filtered off with suction, washed with isopropanol and diethyl ether and dried in a desiccator. The yield over stages 1b and 1c is 2.9 g. (72.7% of theory); m.p. 175° C.

Analysis:

| calc.: | C 73.2%; | H 7.27%; | N 10.52% |
|---|---|---|---|
| found: | 75.9%; | 7.21%; | 9.999% |

NMR spectrum (hexadeuterodimethyl sulphoxide): CH$_3$-(N-methyl) S 2.83 ppm, —CH (acrylic) Q 5.7 ppm, CH$_2$= (acrylic) P 6.3 ppm, aromatic protons between 6.5 and 7.5 ppm.

(d) 250 mg. (0.001 mol) chloranil are dissolved in 15 ml. tetrahydrofuran and mixed with 0.4 g. (0.001 mol) of the acryloyl compound obtained in (c). The solution immediately becomes blue and, after standing for about 2 hours at ambient temperature, crystallization commences. The reaction mixture is left to stand overnight at ambient temperature, whereafter the crystals are filtered off with suction, washed with tetrahydrofuran and diethyl ether and dried in a desiccator. For further purification, the product is taken up in water, neutralized with hydrochloric acid and then shaken out with ethyl acetate. The pure product is precipitated out from the aqueous solution by the addition of sodium chloride. The yield is 0.335 g. (84.2% of theory). In the NMR spectrum of (d), in comparison with (c), there is observed a displacement of the n-methyl proton signal to 3.3 ppm.

EXAMPLE 4

Preparation of acryloylaminophenyl neutral red.

(a) 6.9 g. (0.05 mol) 4-Nitroaniline are dissolved in 150 ml. tetrahydrofuran/chloroform (1:1 v/v) and mixed with a spatula tip of 1,3-dinitrobenzene and with 8 ml. triethylamine. 9 ml. (0.1 mol) acryloyl chloride are slowly added dropwise at 10°-20° C., while stirring. The solution is stirred overnight at ambient temperature, triethylammonium chloride thereby crystallizing out. The tetrahydrofuran/chloroform mixture is then evaporated off in a vacuum at 50° C. and the residue is triturated with water, filtered off with suction and washed with water, isopropanol and diethyl ether. The product is dried in a vacuum at 50° C.

(b) 2.5 g. of the acryloyl compound obtained in (a) are dissolved in 60 ml. tetrahydrofuran at 50° C., while stirring, and diluted with 60 ml. glacial acetic acid (99%) and cooled to 30° C. Subsequently, 10 g. zinc dust are added portionwise, the temperature, even with ice cooling, thereby increasing to 35°-40° C. The reaction mixture is thereafter stirred for 10 minutes at ambient temperature and excess zinc is filtered off with suction and washed with glacial acetic acid. The filtrate is evaporated in a vacuum at 45° C. The oily evaporation residue is chromatographically practically pure and is thus used for the next reaction stage.

(c) A solution of 4.2 g. (0.02 mol) N,N-dimethyl-p-phenylene diammonium dichloride and 2.88 g. (0.02 mol) o-toluidinium chloride in 400 ml. water are slowly mixed, while stirring, at ambient temperature, with a solution of 12 g. (0.04 mol) sodium chromate in 100 ml. water. The green product which separates out is, after 15 minutes, filtered off with suction and washed three times with water, the wash solution thereby remaining green. The precipitate is then immediately further worked up by suspending it in a comparatively small amount of water and homogenizing. The homogeneous suspension is diluted with water to 1.6 liters. After the addition of 1.15×0.02 mol N-acryloyl-p-phenylene diammonium acetate in 100 ml. water, the reaction mixture is adjusted to pH 4.9 with 130 ml. 3 M sodium acetate solution. Subsequently, the mixture is heated to the boil, while stirring. The solution thereby first becomes deep blue and then, upon boiling, dark violet (for completion of the reaction, it is boiled for 5 minutes). Subsequently, the boiling hot solution is suction filtered through a filter funnel and the filtrate (about 2 liters) is adjusted with 240 g. sodium chloride to a 2 M solution and left to stand overnight in a refrigerator. The precipitated crystals are filtered off with suction and dried in a desiccator (it must not be washed with water since the substance is readily soluble in water). 2.4 g. of crude product are obtained.

For further purification, 1.3 g. of the crude product are dissolved in 25 ml. methanol and 0.1 M sodium chloride solution (4:1 v/v) and applied to a silica gel 60 column (4×95 cm.). The column is then eluted with the same solvent (fraction volumes 2 ml.). Fractions 22-55 are combined and evaporated in a vacuum to about 15 ml. The crystals obtained are filtered off with suction, washed with a little 0.1 M sodium chloride solution and dried in a desiccator. There is obtained 0.665 g. of chromatographically pure dyestuff.

EXAMPLE 5

Preparation of 9-(acryloylaminoethylamino)-3-chloro-7-methoxyacridine.

854 mg. 3,9-Dichloro-6-methoxyacridine are heated in an oilbath at 60° C. for 30 minutes with 1 ml. ethylenediamine and 7.7 g. phenol. The melt is taken up in 200 ml. chloroform and 150 ml. water, adjusted to pH 4 with acetic acid and equilibrated. The organic phase is subsequently extracted 3 or 4 times with 0.1 M sodium acetate buffer and then discarded.

The aqueous extracts are adjusted to pH 9.5 with an aqueous solution of sodium carbonate, extracted with chloroform-n-butanol (20:1 v/v) and the organic phase filtered over silicone paper and evaporated in a vacuum. The residue is dissolved in 0.1 M sodium acetate buffer, residues of dimerised product are filtered off and the solution is adjusted to pH 10. After 1 hour at ambient temperature, the precipitate is filtered off, washed with a little dilute ammonia solution at 4° C. and dried. The yield is 50-80% of theory.

206 mg. of the amino compound obtained are dissolved in 25 ml. chloroform with warming and, after cooling, mixed with 0.3 ml. acrylic chloride, the solution immediately becoming darker in colour. After a few minutes, the acryloyl derivative precipitates out. After filtering off with suction and washing with some chloroform, there are obtained 122 mg. (50% of theory) 9-(acryloylaminoethylamino)-3-chloro-7-methoxyacridine in chromatographically pure form.

It will be understood that the specification and examples are illustrative, but not limitative of the present invention, and that other embodiments within the spirit and scope of the invention will suggest themselves to those skilled in the art.

What is claimed is:

1. Process for the preparation of an adsorbent for the affinity-specific separation of nucleic acids, comprising a polymeric carrier material onto which an affine residue group consisting of a base and/or structure specific complex former for nucleic acids, is covalently bound wherein said polymeric carrier material is first formed from at least one monomer which additionally possesses a functional group via which the affine residue for the biopolymer can be bound directly or via a polymeric spacer, the polymeric carrier material is optionally comminuted to the desired particle size and then the affine residue for the biopolymer is grafted on either directly or by copolymerization in the presence of at least one further monomer as co-monomer so that particles of the desired size are produced.

2. Process as claimed in claim 1 wherein the affine residue for the biopolymer having a copolymerizable double bound is grafted on to poly-bisacrylamide in the presence of an excess of a further copolymerizable monomer as co-monomer.

3. Process as claimed in claim 1 wherein the graft copolymerization is carried out in water or in an inert solvent in the presence of a conventional polymerization catalyst.

4. Process as claimed in claim 1 wherein the affine residue for the biopolymer having a copolymerizable double bond is acrylic-phenyl neutral red or acrylic-malachite green and the further copolymerizable monomer used is acrylamide.

5. Process as claimed in claim 1 wherein a copolymer of acrylamide and acrylic-phenyl neutral red or acrylic-malachite green with a degree of polymerization of 200 to 300 is grafted on.

6. Process as claimed in claim 1 wherein the affine residue for the biopolymer having a copolymerizable double bond and the further copolymerizable monomer are used in a weight ratio of 1:100 to 1:5000.

7. Process as claimed in claim 6 wherein the said weight ratio is preferably 1:3000.

* * * * *